United States Patent [19]

Niwa et al.

[11] Patent Number: 6,087,527

[45] Date of Patent: Jul. 11, 2000

[54] METHOD FOR PRODUCING ALKYL CARBOXYLATES BY MULTI-STAGE ESTERIDICATION INTERRUPTED WITH A DEHYDRATION STEP

[75] Inventors: Atsushi Niwa, Kyoto; Shinzo Imamura, Aichi; Akio Hasebe; Ito Nobuhiko, both of Chiba, all of Japan

[73] Assignees: Toray Industries, Inc.; Soda Aromatic Co., Ltd., both of Japan

[21] Appl. No.: 09/043,254

[22] PCT Filed: Jul. 17, 1997

[86] PCT No.: PCT/JP97/02488

§ 371 Date: Sep. 21, 1998

§ 102(e) Date: Sep. 21, 1998

[87] PCT Pub. No.: WO98/03460

PCT Pub. Date: Jan. 29, 1998

[30] Foreign Application Priority Data

Jul. 18, 1996 [JP] Japan ..................................... 8-207736

[51] Int. Cl.[7] .......................... C07C 69/34; C07C 69/02; C07C 69/00

[52] U.S. Cl. .................................. 560/190; 560/8; 560/76; 560/96; 560/129; 560/231

[58] Field of Search .................................. 560/190, 8, 76, 560/96, 129, 231

[56] References Cited

PUBLICATIONS

Melvin Newman; An Advanced Organic Laboratory Course; Macmillan, New York; pp. 8–11, 1972.

*Primary Examiner*—Gary Geist
*Assistant Examiner*—Robert W. Deemie
*Attorney, Agent, or Firm*—Austin R. Miller

[57] ABSTRACT

Method for producing an alkyl carboxylate, in which a carboxylic acid and an alcohol are esterified by reaction in the presence of an acid catalyst, by removing water in a dehydration step established halfway in the esterification reaction using a solid acid catalyst as the acid catalyst, and restarting the esterification reaction to complete the esterification reaction.

11 Claims, No Drawings

METHOD FOR PRODUCING ALKYL CARBOXYLATES BY MULTI-STAGE ESTERIDICATION INTERRUPTED WITH A DEHYDRATION STEP

TECHNICAL FIELD

The present invention relates to a method for producing an alkyl carboxylate from a carboxylic acid and an alcohol. The present invention is especially suitable for producing an alkanedioic acid dialkyl ester using an alkanedioic acid as the carboxylic acid, and the alkanoedioic acid dialkyl ester can be suitably used as an intermediate product of drugs, agricultural chemicals, perfumes, dyes, liquid crystal materials, high molecular materials, etc.

BACKGROUND ARTS

As a method for producing an alkanedioic acid dialkyl ester in the presence of an acid catalyst, it is known to esterify an alkanedioic acid and a monohydric alcohol in the presence of sulfuric acid (Japanese Patent Laid-Open (Kokai) No. 63-243060). Furthermore, as a method for producing an ester using a solid acid catalyst, it is known to esterify a carboxylic acid and an alcohol using an ion exchange resin as a catalyst (Japanese Patent Laid-Open (Kokai) No. 63-297340).

However, according to the production method of Japanese Patent Laid-Open (Kokai) No. 63-243060, the gross yield of the alkanedioic acid dialkyl ester is as low as about 85 to 95% and the purity is as low as about 90 to 98%. Furthermore, the isolation and purification of the produced alkanedioic acid dialkyl ester requires a step of neutralizing the acid catalyst by an alkali and a step of distillation in a high vacuum of about 13 to 53 Pa (0.1 to 0.4 Torr) in a high temperature range of 117° C. to 201° C., and the method does not allow a highly pure alkanedioic acid dialkyl ester to be obtained economically at a high yield.

DISCLOSURE OF THE INVENTION

The inventors studied intensively to solve these problems, and as a result, found that an alkanedioic acid dialkyl ester can be obtained at a high purity of 99% or more with the amount of the alcohol used kept smaller, by removing the water produced in the reaction system in a dehydration step established halfway in the esterification reaction and restarting the esterification reaction, to complete the esterification reaction.

Furthermore, they found that if a solid acid catalyst is used as the acid catalyst, the produced alkanedioic acid dialkyl ester can be easily separated from the acid catalyst. Thus, the present invention has been completed.

The present invention is a method for producing an alkyl carboxylate, in which a carboxylic acid and a monohydric alcohol are esterified by reaction in the presence of an acid catalyst, comprising the steps of removing the reaction solution from contact with the acid catalyst and removing the water produced in the reaction system in a dehydration step established halfway in the esterification reaction, with the reaction solution kept away from contact with the acid catalyst, and restarting the esterification reaction, in the presence of the acid catalyst to complete the esterification reaction.

THE MOST PREFERRED EMBODIMENTS OF THE INVENTION

In the present invention, it is preferable to conduct the dehydration step when the reaction solution is kept away from contact with the acid catalyst. If the dehydration step is established with the reaction solution kept in contact with the acid catalyst, an ester hydrolyzing reaction may occur and this will lower the ester yield.

In the present invention, the method for keeping the reaction solution away from contact with the catalyst halfway in the esterification reaction is not especially limited. Neutralization or filtration, etc. can be used.

In the present invention, the number of dehydration steps established in the esterification reaction is not especially limited, but it is preferable that the number of dehydration steps is 1 to 3 in view of working efficiency. If the number of dehydration steps is 4 or more, the working efficiency tends to decline.

In the present invention, as for the timing of the aforementioned dehydration step or steps established in the esterification reaction, when the number of dehydration steps established halfway in the esterification reaction is one, the time when the conversion of the alkanedioic acid into the alkanedioic acid dialkyl ester has become 85 to 95%, especially 90 to 94% is preferable for decreasing the amount of the alcohol used. Thus, the dehydration step takes place partway through the reaction but not necessarily halfway.

In the present invention, the dehydration method in the dehydration step is not especially limited, and can include distilling away under reduced pressure, separation, centrifugation, or contact with a dehydrating agent such as a molecular sieve or magnesium sulfate, etc.

In the present invention, as for the degree of dehydration in the dehydration step, it is preferable to dehydrate until the water content of the reaction mixture becomes 0.5% or less, especially 0.1% or less when the esterification reaction is restarted, since the amount of the alcohol used can accordingly be kept smaller.

The acid catalyst used in the present invention is preferably a solid acid catalyst. The solid acid catalysts which can be used here include silica gel, alumina, zeolite, heteropolyacids, weak acid ion exchange resins and strong acid ion exchange resins. Especially strong acid ion exchange resins are preferable.

Strong acid ion exchange resins especially preferably used in the present invention are benzenesulfonic acid type ion exchange resins. Such strong acid ion exchange resins include, though not limited to, "Diaion" SK series, trade name, produced by Mitsubishi Kagaku, "Diaion" PK series, trade name, produced by Mitsubishi Kagaku, "Amberlite" IR-120B, trade name, produced by Organo, "Amberlist" 15E, trade name, produced by Organo, "Dowex" 50W series, trade name, produced by Dow Chemical, etc. Among them, preferable are "Diaion" PK series, and especially preferable is "Diaion" PK-220-H. These strong acid ion exchange resins can also be used as a mixture.

The strong acid ion exchange resins preferably used in the present invention can be regenerated, as required, by interaction with a mineral acid such as sulfuric acid, hydrochloric acid or nitric acid.

The carboxylic acids which can be preferably used in the present invention are alkanedioic acids represented by the general formula HOOC—X—COOH (where X stands for a straight chain, branched chain or cyclic alkyl chain with 6 to 14 carbon atoms). Such alkanedioic acids include straight chain alkanedioic cids such as octanedioic acid, nonanedioic acid, decanedioic acid, undecanedioic acid, dodecanedioic acid, tridecanedioic acid, tetradecanedioic acid, pentadecanedioic acid and hexadecanedioic acid; branched chain alkanedioic acids such as methyloctanedioic acid, ethyloctanedioic acid, methylnonanedioic acid, ethylnonanedioic acid, methyldecanedioic acid, ethyldecanedioic acid, methylundecanedioic acid, ethylundecanedioic acid, methyldodecanedioic acid, ethyldodecanedioic acid, methyltridecanedioic acid, ethyltridecanedioic acid, methyltetradecanedioic acid, ethyltetradecanedioic acid and methylpentadecanedioic acid; and cycloalkanedicarboxylic acids such as cyclobutanediacetic acid, cyclohexanedicarboxylic acid, cyclohexanediacetic acid and bicyclohexanedicarboxylic acid. Among them, preferable are decanedioic acid, undecanedioic acid, dodecanedioic acid, tridecanedioic acid and tetradecanedioic acid.

It is preferable that the monohydric alcohol used in the present invention is a straight chain or branched chain monohydric alcohol with 1 to 4 carbon atoms. Such preferable monohydric alcohols include methanol, ethanol, 1-propanol, 2-propanol, 1-butanol, 2-butanol, 2-methyl-1-propanol and 2-methyl-2-propanol. Among them, more preferable are methanol and ethanol.

The reaction temperature of the present invention is usually 50 to 100° C., but a range of 60 to 80° C. is preferable. If the reaction temperature is lower than 50° C., the reaction does not proceed sufficiently to lower the yield. If the reaction temperature exceeds 100° C., the acid catalyst may be inactivated.

The reaction pressure of the present invention can be changed in a range of 0.05 to 0.5 MPa (0.5 to 5 atmospheric pressure), but a range of 0.1 to 0.2 MPa (1 to 2 atmospheric pressure) is preferable.

The reaction of the present invention can be effected by the batch method or the flow method.

When the reaction of the present invention is effected by the batch method, the ratio of the weight of the alkanedioic acid:the weight of the monohydric alcohol:the volume of the acid catalyst depends on the number of dehydration steps established in the esterification reaction, their timings and the final yield of the alkanedioic acid dialkyl ester. If only one dehydration step is established halfway in the esterification reaction at a point where the conversion into the alkanedioic acid dialkyl ester reaches 93%, to achieve a final alkanedioic acid dialkyl ester yield of 99%, it is preferable that the ratio of the weight of the alkanedioic acid:the weight of the monohydric alcohol:the volume of the acid catalyst in the first step of reaction is in a range of 1:(0.8–4):(0.5–10) [g/ml], and that the ratio of the weight of the alkanedioic acid:the weight of the monohydric alcohol:the volume of the acid catalyst in the second step of reaction is in a range of 1:(0.8–2):(0.5–10) [g/ml]. If the amount of the monohydric alcohol is smaller than the above range, the yield of the alkanedioic acid dialkyl ester is too low, and if larger than the above range, the excessive amount of the monohydric alcohol must be removed when the alkanedioic acid dialkyl ester is purified, to require a longer time and larger equipment. If the amount of the acid catalyst is smaller than the above range, the reaction progresses so slowly as to lower the yield of the alkanedioic acid dialkyl ester, and if larger than the above range, the amount of the alkanedioic acid dialkyl ester produced per unit amount of catalyst declines inefficiently.

It is more preferable that the ratio of the weight of the alkanedioic acid:the weight of the monohydric alcohol:the volume of the acid catalyst in the first step of the reaction is in a range of 1:(1–2):(2–5) [g/ml] and that the ratio of the weight of the alkanedioic acid:the weight of the monohydric alcohol:the volume of the acid catalyst in the second step of the reaction is in a range of 1:(1–1.5):(1–3) [g/ml].

When the reaction of the present invention is effected according to the flow method, the ratio by weight of the alkanoic diacid : the monohydric alcohol depends on the number of dehydration steps to be established during the esterification reaction, their timings and the final alkanedioic acid dialkyl ester yield. If only one dehydration step is established in the esterification reaction at a point where the conversion into the alkanedioic acid dialkyl ester reaches 93%, to achieve a final alkanedioic acid dialkyl ester yield of 99%, it is preferable that the ratio by weight of the alkanedioic acid:the monohydric alcohol in the first step of reaction is in a range of 1:(2–4), and that the ratio by weight of the alkanedioic acid:the monohydric alcohol in the second step of the reaction is in a range of 1:(0.8–2). In this case, the SV value showing the amount of reaction solution flow depends on the ratio by weight of the alkanedioic acid to the monohydric alcohol, but it is preferable that SV is in a range of 0.3 to 0.8/h in both the first and second steps of the reaction. If the amount of the monohydric alcohol is smaller than the above range, the yield of the alkanedioic acid dialkyl ester declines, and the solubility of the alkanedioic acid becomes so low as to make the execution of the flow method difficult. If it is larger than the above range, an excessive amount of the monohydric alcohol must be removed when the alkanedioic acid dialkyl ester is purified, requiring a longer time and larger equipment. If the SV value is larger than the above range, the reaction does not proceed sufficiently to lower the yield, and if the SV value is smaller than the above range, the amount of the alkanedioic acid dialkyl ester produced per unit of time becomes small inefficiently.

It is more preferable that the ratio by weight of the alkanedioic acid:the monohydric alcohol in the first step of the reaction is in a range of 1:(3–4), and that the ratio by weight of the alkanedioic acid:the monohydric alcohol in the second step of the reaction is in a range of 1:(1–1.2). It is more preferable that the SV value is in a range of 0.4 to 0.6/h in both the first and second steps of the reaction.

When the reaction of the present invention is effected according to the batch method, the solid acid catalyst can be separated by filtration after completion of the esterification reaction, and from the obtained filtrate, the unreactive monohydric alcohol and produced water can be distilled away at atmospheric pressure or under reduced pressure, to isolate the alkanedioic acid dialkyl ester.

When the reaction of the present invention is effected according to the flow method, the unreactive monohydric alcohol and produced water can be distilled away at atmospheric pressure or under reduced pressure from a reaction solution which has passed through a solid acid catalyst tank, to isolate the alkanedioic acid dialkyl ester.

The alkanedioic acid dialkyl esters obtained in the present invention can be suitably used as intermediates of drugs, agricultural chemicals, perfumes, dyes, liquid crystal materials, high molecular materials, etc., and typically preferably used as raw materials for obtaining large cyclic lactones used for perfumes.

EXAMPLES

The present invention is described below concretely in reference to examples of the present invention and comparative examples, but is not limited thereto or thereby.

Example 1

Marketed ion exchange resin "Diaion" PK-220 was regenerated into the acid type by 2N hydrochloric acid.

A 200 ml three-neck flask with a reflux condenser was charged with 10 g of dodecanedioic acid, 10 g of methanol and 20 ml of the regenerated "Diaion" PK-220, and the mixture was stirred by a mechanical stirrer, while being refluxed (64° C.) for 6 hours. The reaction solution was analyzed by gas chromatography, and it was found that the conversion of dodecanedioic acid into dodecanedioic acid dimethyl ester was 90.12%. The reaction solution was filtered, and the obtained filtrate was concentrated under reduced pressure by a rotary evaporator, to obtain 11.10 g of a residue as a colorless solid. The water content of the residue was 0.1%.

The residue thus obtained was put into a 200 ml three-neck flask with a reflux condenser, together with 10 g of methanol and 20 ml of the reproduced PK-220, and the mixture was stirred by a mechanical stirrer, while being refluxed (64° C.) for 6 hours. The reaction solution was analyzed by gas chromatography, and it was found that the conversion from dodecanedioic acid into dodecanedioic acid dimethyl ester was 99.23%. The reaction solution was filtered, and the obtained filtrate was concentrated under reduced pressure by a rotary evaporator, and dried by a vacuum dryer for 4 hours, to obtain 11.22 g of a residue as a colorless solid. The residue was analyzed by gas chromatography, and it was found that the purity of dodecanedioic acid dimethyl ester was 99.19%. The yield of dodecanedioic acid dimethyl ester obtained from the purity was 99.20%.

Example 2

A stainless steel tube with a diameter of 12 mm and a length of 200 mm open at both the ends was packed with 17 ml of the "Diaion" PK-220 reproduced as described in Example 1, and placed in a 60° C. thermostatic oven.

A solution with 10 g of dodecanedioic acid dissolved in 40 g of methanol was passed through said stainless steel tube by a fixed delivery pump at a rate of 8.5 ml per hour (SV=0.5/h). The liquid flowing out of the stainless steel tube was collected and analyzed by gas chromatography, and it was found that the conversion of dodecanedioic acid into dodecanedioic acid dimethyl ester was 93.17%. The liquid was concentrated under reduced pressure, to obtain 11.14 g of a residue as a colorless solid. The water content of the residue was 0.1%.

The residue obtained as above was dissolved into 10 g of methanol, and the solution was passed through said stainless steel tube by a fixed delivery pump at a rate of 8.5 ml per hour (SV=0.5/h). The liquid flowing out of the stainless steel tube was collected and analyzed by gas chromatography, and it was found that the conversion of dodecanedioic acid into dodecanedioic acid dimethyl ester was 99.21%. The liquid was concentrated under reduced pressure by a rotary evaporator and dried by a vacuum dryer for 4 hours, to obtain 11.21 g of a residue as a colorless solid. The residue was analyzed by gas chromatography, and it was found that the purity of dodecanedioic acid dimethyl ester was 99.25%. The yield of dodecanedioic acid dimethyl ester obtained from the purity was 99. 17%.

Comparative Example 1

A 200 ml three-neck flask with a reflux condenser was charged with 10 g of dodecanedioic acid, 80 g of methanol and 50 ml of the reproduced "Diaion" PK-220, and the mixture was stirred by a mechanical stirrer while being refluxed (64° C.) for 6 hours. The reaction solution was analyzed by gas chromatography, and it was found that the conversion of dodecanedioic acid into dodecanedioic acid dimethyl ester was 99.17%. The reaction solution was filtered, and the obtained filtrate was concentrated under reduced pressure by a rotary evaporator and dried by a vacuum dryer for 4 hours, to obtain 11.21 g of a residue as a colorless solid. The residue was analyzed by gas chromatography, and it was found that the purity of dodecanedioic acid dimethyl ester was 99.16%. The yield of dodecanedioic acid dimethyl ester obtained from the purity was 99.08%.

Comparative Example 2

A stainless steel tube with a diameter of 12 mm with a length of 200 mm open at both the ends was packed with 17 ml of the reproduced "Diaion" PK-220, and placed in a 60° C. thermostatic oven.

A solution with 10 g of dodecanedioic acid dissolved in 80 g of methanol was passed through said stainless steel tube at a rate of 7 ml per hour (SV=0.41/h). The liquid flowing out of the stainless steel tube was collected and analyzed by gas chromatography, and it was found that the conversion of dodecanedioic acid into dodecanedioic acid dimethyl ester was 99.11%. The liquid was concentrated under reduced pressure by a rotary evaporator and dried by a vacuum dryer for 4 hours, to obtain 11.21 g of a residue as a colorless solid. The residue was analyzed by gas chromatography, and it was found that the purity of dodecanedioic acid dimethyl ester was 99.07%. The yield of dodecanedioic acid dimethyl ester obtained from the purity was 98.99%.

Industrial applicability

According to the present invention, the amount of the alcohol used can be decreased, and a highly pure alkanoic diacid dialkyl ester can be produced at a high yield. The alkanoic diacid dialkyl esters produced according to the present invention can be suitably used as intermediates of drugs, agricultural chemicals, perfumes, dyes, liquid crystal materials, high molecular materials, etc.

We claim:

1. A method for producing an alkyl carboxylate, in which a carboxylic acid and an alcohol are esterified in a reaction solution in the presence of an acid catalyst, comprising the steps of partially completing the esterification reaction, interrupting the esterification reaction, removing water from said reaction solution while said esterification remains interrupted, said water removal being effected in one or more dehydration steps established during the esterification reaction, and restarting the esterification reaction by contact with acid catalyst to complete the esterification reaction.

2. A method for producing an alkyl carboxylate, in which an alkanedioic acid and an alcohol are esterified by reaction in the presence of an acid catalyst, comprising the steps of interrupting the esterification reaction, removing water from the reaction solution by dehydration and restarting the esterification reaction to complete the esterification reaction.

3. A method for producing an alkyl carboxylate, according to claim 1 or 2, wherein the dehydration step is established with the reaction solution kept away from contact with the acid catalyst.

4. A method for producing an alkyl carboxylate, according to claim 1 or 2, wherein the dehydration is performed in one or more additional dehydration steps.

5. A method for producing an alkyl carboxylate, according to claim 1 or 2, wherein in the dehydration step, water is removed until the water content of the reaction mixture becomes 0. 5% or less after which the ester if i cat ion react ion is restarted.

6. A method for producing an alkyl carboxylate, according to claim 2, wherein the acid catalyst is a solid acid catalyst.

7. A method for producing an alkyl carboxylate, according to claim 1, wherein the solid acid catalyst is a strong acid ion exchange resin.

8. A method for producing an alkyl carboxylate, according to claim 2, wherein the alkanedioic acid is represented by the general formula HOOC—X—COOH, where X stands for a straight chain, a branched chain or a cyclic alkyl chain having 6 to 14 carbon atoms.

9. A method for producing an alkyl carboxylate, according to claim 1 or 2, wherein the alcohol is a monohydric alcohol.

10. A method for producing an alkyl carboxylate, according to claim 9, wherein the monohydric alcohol is a straight chain or branched chain monohydric alcohol with 1 to 4 carbon atoms.

11. A method for producing an alkyl carboxylate, according to claim 9, wherein the monohydric alcohol is a monohydric alcohol with a boiling point lower than that of water.

* * * * *